United States Patent [19]

Leacock

[11] 4,092,132
[45] May 30, 1978

[54] RECOVERY OF METHACROLEIN

[75] Inventor: James Leacock, New York, N.Y.

[73] Assignee: Halcon Research and Development Corp., New York, N.Y.

[21] Appl. No.: 830,737

[22] Filed: Sep. 6, 1977

[51] Int. Cl.² ............................................. B01D 19/00
[52] U.S. Cl. ............................................. 55/48; 55/56; 55/84
[58] Field of Search ................. 55/37, 46, 48, 56, 84; 260/604 R

[56] References Cited

U.S. PATENT DOCUMENTS

| | | | |
|---|---|---|---|
| 3,162,514 | 12/1964 | Rollen et al. | 55/48 X |
| 3,499,038 | 3/1970 | McDaniel et al. | 260/604 R |
| 3,627,701 | 12/1971 | Coyne et al. | 260/604 R X |
| 3,761,516 | 9/1973 | Khoobiar | 260/530 N |
| 3,828,099 | 8/1974 | Sato et al. | 55/46 X |
| 3,972,920 | 8/1976 | Ishii et al. | 260/604 R X |

Primary Examiner—Charles N. Hart
Assistant Examiner—Richard W. Burks
Attorney, Agent, or Firm—William C. Long; David Dick; Riggs T. Stewart

[57] ABSTRACT

Methacrolein is recovered from a gaseous mixture containing it by bringing the gaseous mixture into contact with acetic acid.

3 Claims, 1 Drawing Figure

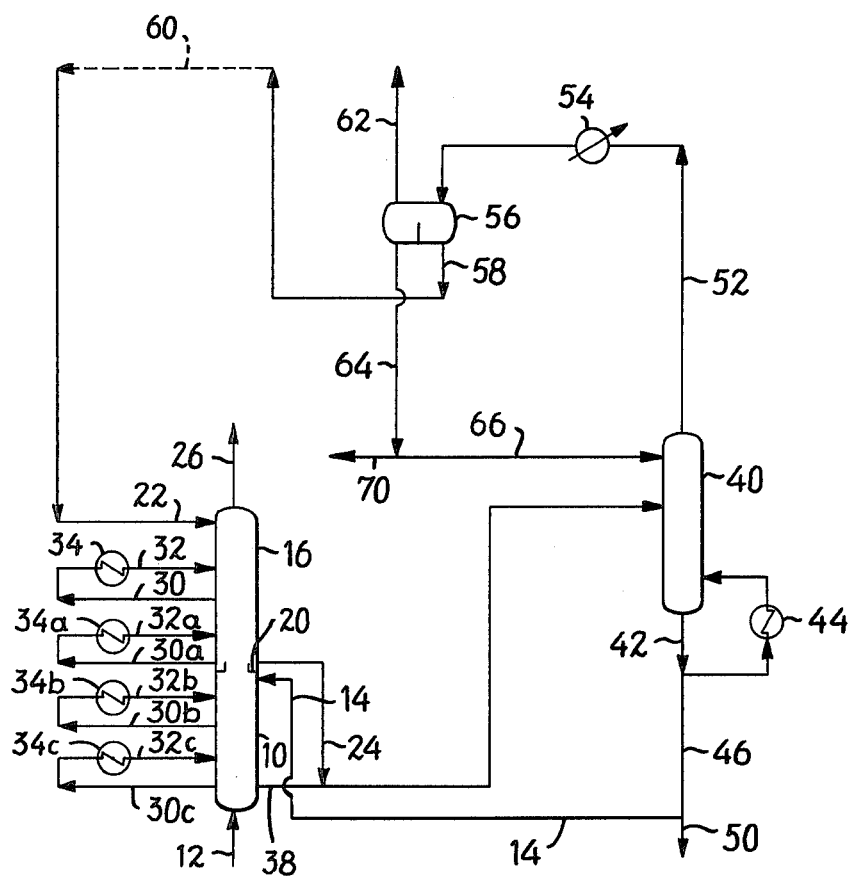

RECOVERY OF METHACROLEIN

This invention relates to the recovery of methacrolein from a vapor stream containing it in admixture with isobutylene, oxygen, nitrogen, carbon-dioxide and other inert gases.

The preparation of methacrolein by the catalytic oxidation of isobutylene, or of tertiary butyl alcohol, which is dehydrated to isobutylene in the reaction zone, is a known reaction described, for example, in Ishii et al., U.S. Pat. No. 3,972,920. In processes of this type, isobutylene or tertiary butyl alcohol are typically mixed with oxygen, an inert gas such as nitrogen, carbon dioxide and the like, and steam, and the resulting mixture is oxidized at temperatures generally ranging between 300° and 500° C in the presence of a suitable catalyst such as the one described in the above-mentioned patent, the gaseous reaction product comprising, in addition to methacrolein, unreacted oxygen, large amounts of inert gas and steam and minor amounts of organic by-products such as aldehydes, aliphatic acids, ketones, and the like. In some known processes for the recovery of the product methacrolein, which is in rather low concentration, e.g. less than 5 volume %, generally 2–3%, the gaseous reaction mixture is treated in order to concentrate the methacrolein by condensing the water contained in the gaseous effluent. For this purpose the effluent is subjected to a series of cooling stages, for example as described in Roelen et al., U.S. Pat. No. 3,162,514. An improved process for separating water from the catalytic reactor effluent is described in my co-pending application entitled "Treatment of Methacrolein-containing Gases" being filed on even date herewith and identified as Case 1121, the disclosure of which application is incorporated herein by reference.

Subsequently, the thus substantially dehydrated gaseous mixture, which contains methacrolein but which also contains the non-condensed gases, e.g. isobutylene, oxygen, inert gases such as nitrogen and carbon dioxide, and the like, must be treated to recover the methacrolein from it. It has been proposed to absorb or "scrub" the vapors with an organic solvent which will selectively dissolve the methacrolein and from which the methacrolein may later be separated. Various solvents have been disclosed for this purpose. Sato et al. in U.S. Pat. No. 3,828,099, for example, propose the use of an alcohol, e.g. methanol, ethanol and isopropanol, or acetone or acetonitrile, whereas in Roelen et al. U.S. Pat. No. 3,162,514, the absorbing or scrubbing of the methacrolein is effected by means of a ketone such as ethyl amyl ketone, diisobutyl ketone, methyl amyl ketone, as well as mesityl oxide. On the other hand, Roelen et al. U.S. Pat. No. 3,218,357 proposes the recovery of methacrolein by subjecting a gaseous mixture to contact with certain branched-chain hydrocarbons, e.g. those having 6 to 20 carbon atoms, preferably 9 to 15.

While these various absorption or scrubbing systems are relatively effective, they require large amounts of absorbing solvent in order to recover the methacrolein to a sufficient extent to be economically attractive. Furthermore, methacrolein produced by catalytic oxidation of isobutylene or tertiary butyl alcohol as described above, and subsequently recovered by scrubbing, e.g. by the procedures disclosed in the above mentioned patents, is generally subsequently converted to methacrylic acid by subjecting it, in appropriate admixture with oxygen and inert gas, to catalytic oxidation, for example as described in Khoobiar U.S. Pat. No. 3,761,516.

The presence of contaminants such as the alcohols, ketones and hydrocarbons of the type described in the methacrolein supplied to such a catalytic oxidation, tent to have an adverse effect upon the reaction. It is accordingly considered necessary to remove these solvents from the methacrolein to a very high degree, which complicates the process and is economically disadvantageous. Furthermore, the isobutylene and other gases are at least in part recycled to the catalytic oxidation to produce additional quantities of methacrolein and if they contain significant amounts of the added solvents, these contaminants have an adverse effect upon this reaction. Consequently, these gases must be carefully treated to free them from the solvent vapors which inevitably are contained in the uncondensed gaseous mixture before the mixture can be recycled.

It is an object of this invention to provide an improved process for absorbing or scrubbing methacrolein from gaseous mixtures containing it.

It is a further object of the invention to provide an improved process of the character indicated which requires the use of relatively small quantities of absorbing liquid for effective recovery of the methacrolein.

It is a still further object of the invention to provide a process for recovering methacrolein from gaseous admixtures containing isobutylene which does not contaminate the methacrolein, or the isobutylene recovered for recycling, with foreign organic compounds which may adversely affect the subsequent conversion of the methacrolein to methacrylic acid or the conversion of the isobutylene to additional methacrolein.

In accordance with the invention, gaseous mixture containing methacrolein and isobutylene are subjected to treatment, e.g. by countercurrent contact, with acetic acid. It has been surprisingly discovered that acetic acid is an unusually effective absorbent for methacrolein and can be readily separated from it by conventional fractional distillation. Moreover, in the catalytic oxidation of methacrolein to produce methacrylic acid, and in the oxidation of isobutylene or tertiary butyl alcohol to methacrolein, small amounts of acetic acid are produced so that acetic acids is thus a material which is indigenous to the system. Consequently, small amounts of acetic acid can be readily tolerated in the methacrolein fed to the catalytic oxidation reaction to convert the methacrolein to methacrylic acid, and in the recycle gases fed to the catalytic oxidation reaction to produce methacrolein, so that the problem of freeing the methacrolein or the recycle gases from added foreign contaminants, such as the scrubbing solvents used in the prior art, is avoided.

The scrubbing of the methacrolein-containing gaseous mixture can be effected in one or more steps, but one step is generally sufficient. The scrubbing is preferably effected countercurrently although co-current contact can also be employed, but is less desirable. The zone in which the contact between the acetic acid and the gaseous mixture takes place can be of any conventional type suitable for gas-liquid contact, but suitably it is filled with bodies providing additional surfaces such as Raschig rings or it may be provided with bubble cap trays, trickle trays, sieve trays, valve trays, and the like.

The methacrolein is effectively absorbed by the acetic acid in the scrubbing zone, but the remaining components of the gaseous mixture subjected to treatment, including isobutylene, will tent to contain some acetic acid. However, as previously mentioned, one of the important advantages of the process of this invention is that the acetic acid is not a foreign contaminant, and even if the isobutylene contained in the gases recovered for recycle to the catalytic reactor for conversion to additional quantities of methacrolein contains some acetic acid, there is no adverse effect upon the catalytic reaction. It is desirable, however, that the acetic acid content of the exiting gases from the methacrolein scrubber be kept within reasonable limits since the acetic acid is required for eventual recycling to the scrubber and acetic acid removed in the exiting gases must, of course, be replaced in order to maintain a constant volume of scrubber liquid. Consequently, it is preferable to maintain the amount of acetic acid in the gaseous mixture below about 0.5 volume %. For this purpose, the acetic acid can be readily removed from the gases by contact with water, e.g. countercurrent contact. This contact can be effected in a separate scrubbing zone through which the gases leaving the methacrolein scrubber are passed in countercurrent contact but preferably, and most conveniently, the acetic acid scrubber and the methacrolein scrubber are interconnected, the former above the latter, with the gases leaving the methacrolein scrubbing zone passing directly into the acetic acid scrubbing zone, into the upper portion of which water is continuously introduced.

The gaseous mixture to be scrubbed is suitably at an elevated pressure in order that it will readily flow through the methacrolein scrubbing zone and the acetic acid scrubbing zone. Ordinarily a pressure of at least about 10 psig is desirable, but most suitably pressures of 100 to 250 psig are advantageous. The upper limit of the pressure is governed primarily by economic considerations. The temperature of the gas is not critical, but it ordinarily should be at least about 50° C and preferably 35° to 45° C and the acetic acid used as absorber liquid is advantageously at a temperature within the range of 35° to 50° C. Preferably, although not necessarily, the acetic acid absorber liquid is maintained at a substantially constant temperature by passing it through cooling means during the course of the scrubbing of the methacrolein. The scrubbing of the acetic acid with water is conducted under temperature conditions corresponding to those used in the methacrolein scrubbing. The methacrolein-containing gas mixture which is fed to the acetic acid-containing scrubbing zone for removal of methacrolein can be the gaseous effluent exiting from the catalytic reactor in which the methacrolein is produced, the mixture being suitably increased in pressure by any convenient means, such as a centrifugal compressor, to the desired pressure for scrubbing. Preferably, however, in order to minimize the amount of acetic acid required, at least some of the water contained in the oxidation reactor effluent is first removed. This can be done in any convenient manner, for example, as described in the above-mentioned Roelen et al. patents, but preferably it is effected by means of the process described in my above-identified co-pending application entitled "Treatment of Methacrolein-containing Gases" wherein the reactor effluent is quenched in aqueous media under gradually increased pressure and a gaseous mixture is recovered which is substantially free from water and, at the same time, has a pressure which is appropriate for being directly fed into the methacrolein scrubbing zone containing acetic acid, in accordance with the process of the present invention. As a general rule, therefore, the feed to the scrubbing zone preferably contains less than about 1 volume % water although, as mentioned, the specific amount of water is not critical from an operational standpoint.

The rate at which the gas to be scrubbed is introduced into acetic acid-containing scrubbing zone will depend upon the water content and the concentration of the methacrolein in the gas as well as upon the type and efficiency of the apparatus defining the scrubbing zone. Consequently, the rate may vary within very wide limits, but typically it will range between 1,000 to 6,000 liters per liter of acetic acid per hour.

From a lower portion of the acetic acid-containing scrubbing zone the acetic acid with its content of absorbed methacrolein is removed and treated in order to separate the acetic acid from the methacrolein. This can be done by ordinary fractional distillation since acetic acid and methacrolein have sufficiently different boiling points that no separation problem arises. In a typical operation, distillation is carried out at a bottoms temperature in the range of 90° to 130° C under a pressure of 6 to 21 psia. The separated acetic acid is withdrawn as bottoms product and the methacrolein passes into the distillate. Ordinarily the liquid effluent from the scrubbing zone in which acetic acid is scrubbed by means of water, as previously described, is combined with the liquid effluent from the lower portion of the methacrolein scrubbing zone and the combined stream is fed to the distillation column for separation of the methacrolein. In this case, both the methacrolein and the water pass into the distillate, which may also contain small amounts of gases such as isobutylene. The distillate from this distillation is condensed and the condensate passed to a phase separator wherein the water and the methacrolein separate into two distinct phases. Part of the thus-obtained methacrolein phase is withdrawn as product for conversion to methacrylic acid or for other uses, and the remainder of the methacrolein phase is returned to the distillation column as reflux to facilitate the distillation in conventional manner, e.g. to provide a reflux ratio of 2:1 to 5:1. The water phase is withdrawn and treated to recover its very minor content of methacrolein or is disposed of in any convenient manner. Advantageously, it may be returned to the acetic acid scrubbing zone as the aqueous scrubbing liquid to remove acetic acid from the gases issuing from the methacrolein-scrubbing zone. Any non-condensed gases such as isobutylene are withdrawn from the phase separator and advantageously recycled to the catalytic reactor for the preparation of additional amounts of methacrolein. Meanwhile, the acetic acid withdrawn from the lower portion of the distillation column is recycled to the methacrolein scrubbing zone and is supplied to that zone to provide the scrubbing liquid for absorption of additional amounts of methacrolein.

The invention will be more fully understood that reference to the accompanying drawing which illustrates, diagrammatically, an illustrative embodiment of a scrubbing and recovery system suitable for carrying out the process of the invention.

Referring to the drawing, the reference numeral 10 designates a scrubber into which the gaseous mixture to be scrubbed is introduced via line 12 and the acetic acid scrubbing liquid is introduced through line 14. In the embodiment illustrated the scrubber 10 is combined with a scrubber 16 from which it is separated by a chimney tray 20 through which the acetic acid-containing gases pass from scrubber 10. Water is introduced into the upper portion of scrubber 16 through line 22 and the resultant water and acetic acid solution formed in the scrubber is withdrawn near its lower end through line 24. The scrubbed gases leave the scrubber 16 through line 26 from which they can be recycled to the catalytic reactor directly or after suitable treatment. As indicated above, it is preferable to maintain the liquid bodies in the scrubbers 10 and 16 at substantially constant temperature, and thus the heat of absorption must be removed in some way. For this purpose, there are provided side stream circuits composed of outlet lines 30, 30a, 30b and 30c connected, respectively, with return lines 32, 32a, 32b and 32c containing, respectively, coolers 34, 34a, 34b and 34c. From the lower portion of the scrubber 10 the acetic acid enriched with absorbed methacrolein is withdrawn through line 38 which joins with line 24 and leads the combined liquid streams to a distillation column 40. Column 40 is provided with a bottoms withdrawal line 42 from which a portion of the bottom stream passes through reboiler 44 for return to the column and the remainder is withdrawn through line 46 for return via line 14 to the upper portion of scrubbing zone 10. If desired, a small amount may be purged through line 50. The vapors from distillation column 40 exit via line 52, pass through condenser 54 and the condensate enters phase separator 56. The aqueous phase is withdrawn via line 58 for removal from the system or, optionally, some or all of it may be returned to the scrubber 16 through line 60. Any non-condensed gases are removed through line 62 while the methacrolein phase is withdrawn through line 64. From line 64 some of the methacrolein is returned to column 40 as reflux through line 66 and the remainder is withdrawn via line 70 as product.

As previously indicated, the drawing is merely an illustrative embodiment of one apparatus system which can be employed in carrying out the process of this invention, but the invention is in no way limited to such an apparatus system and the process of the invention can be applied to various other apparatus systems as will be readily apparent to persons skilled in the art. For example, the scrubbing zones 10 to 16 may be separated from each other and interconnected merely by conduit means. The liquid in line 24 and the liquid in line 38 may be separately treated, if desired, in separate distillations, and numerous other modifications may be made.

The following specific example of practical application of the above-described process will serve to give an even fuller understanding of the invention, but it is to be understood that this example is given by way of illustration only and is not to be construed in any way as limitative of the invention. In the example all parts are by weight, unless otherwise indicated.

EXAMPLE

In a system such as illustrated in the drawing, a gaseous stream is continuously introduced into a vertical scrubbing tower containing 16 theoretical trays or contacting stages, and provided with a chimney tray dividing the tower into approximately equal upper and lower scrubbing sections 16 and 10, respectively. The gaseous stream is fed at the rate of 1,000 parts per hour at a temperature of about 40° C and under a pressure of about 132.3 psig. This gaseous stream represents the vaporous component of the vapor effluent from a representative catalytic oxidation of isobutylene to methacrolein, by means of air in the presence of water vapor, after about 96% of its water vapor content has been removed, e.g. by the process described in the above mentioned co-pending application. It comprises about 5.9% methacrolein, the balance being oxygen, inert gases, unreacted isobutylene and a small amount of water vapor. The gaseous stream is introduced into the bottom of lower section 10 and, at the same time, a stream of acetic acid is introduced at the rate of about 242 parts per hour onto the uppermost tray of lower section 10 of the scrubbing tower and flows countercurrently downwardly to the entering gaseous stream. The entering acetic acid is at a temperature of about 40° C. Water is simultaneously introduced onto the uppermost tray of the upper section 16 of the scrubbing tower at the rate of 10 parts per hour and this water flows downwardly countercurrently to the upwardly flowing gaseous stream passing through the chimney tray 20 from the lower section 10. As a result of passing through the body of acetic acid, 99% of the methacrolein contained in the entering gaseous stream is absorbed and the gaseous stream passes into the upper secton 16 with a content of about 0.5 volume % acetic acid. Contact with the water entering through line 22, however, removes substantially all of the acetic acid so that the scrubbed gaseous stream exiting the scrubber via line 26 contains about 0.06% methacrolein, and 0.03% acetic acid. In the operation of the scrubbing tower the temperature in section 10 is maintained at approximately 40° C and the temperature in section 16 is maintained at about 40° C by passing the flowing liquid through cooling loops arranged as shown in the drawing.

The methacrolein-enriched acetic acid is withdrawn from the lower section 10 of the scrubber and is composed of approximately 73.6% acetic acid and 18.4% methacrolein and flows at the rate of approximately 316 parts per hour. At the same time, from the lower portion of section 16 there is withdrawn a dilute acetic acid stream composed approximately of 40.5% water and 59.6% acetic acid, and this stream is withdrawn at the rate of 14.7 parts per hour. The streams from sections 10 and 16 are combined and fed to the upper portion of fractional distillation column 40 which contains 30 theoretical plates and is operated at a pressure of 12 psia with a bottoms temperature of 120° C and an overhead vapor temperature of 57° C. The vapors leave distillation column 40 at the rate of 200 parts per hour, are condensed and passed to a separator 56 in which they form an aqueous phase and a methacrolein phase. The aqueous phase is withdrawn at the rate of about 11 parts per hour and the methacrolein phase is withdrawn at the rate of about 181 parts per hour. Part of the methacrolein phase is returned to column 40 as reflux to provide a reflux ratio of about 2.3:1, the remainder being withdrawn as product. Non-condensed gases in separator 56 are removed at the rate of 8 parts per hour. Acetic acid is withdrawn from the bottom of column 40 and is recycled to section 10 of the scrubbing tower.

In the foregoing example there is used a scrubber containing 8 theroretical plates in the acetic acid scrubbing zone or section 10 and 8 theoretical plates in the water scrubbing zone or section 16. Ordinarily each scrubbing zone should contain at least 6 theoretical plates or contact stages, preferably 7 to 15 theoretical plates or contact stages. A greater number of plates may be provided, the total number being limited only by practical and economic considerations, as will be apparent to persons skilled in the art. In the example the flow of gas or vapor and acetic acid is such that the L/V ratio, i.e., the ratio of the molar flows of liquid and gas, is 0.13. Ordinarily it should be at least about 0.11, preferably 0.12 to 0.2. Higher ratios can be used but as a general rule economic considerations limit te maximum ratio to about 0.2. The same L/V considerations apply to the water scrubbing zone. Similarly, while it is preferred to maintain the temperature in the scrubbing zones substantially constant, e.g. within a 10° C range, this is by no means essential and cooling means can be omitted altogether with consequent higher L/V's required to maintain equivalent absorption efficiency.

It will, of course, be understood that various changes and modifications may be made with respect to what has been described and illustrated in the drawing without departing from the invention as defined in the appended claims. For example, while the process described involves a sequence of operations carried out under conditions which minimize the possibility of polymerization, a polymerization inhibitor, such as hydroquinone or other inhibitor well known to persons skilled in the art, may be added to any of the streams as desired. It is intended, therefore, that all matter contained in the foregoing description and in the drawing shall be interpreted as illustrative only and not in a limiting sense.

What is claimed is:

1. A process for the recovery of methacrolein from a gaseous mixture which comprises bringing said mixture into contact with a body of acetic acid.

2. A process as defined in claim 1 wherein the gaseous mixture, after passing into contact with said body of acetic acid wherein methacrolein is absorbed from said mixture, is thereafter passed into contact with a body of water.

3. A process as defined in claim 1 wherein the body of acetic acid containing absorbed methacrolein as a result of said contact with the gaseous mixture is fractionally distilled to separate the absorbed methacrolein from the acetic acid.

* * * * *